United States Patent
Schouenborg

(10) Patent No.: US 11,678,907 B2
(45) Date of Patent: Jun. 20, 2023

(54) DEVICE FOR INSERTION INTO NERVOUS TISSUE

(71) Applicant: NEURONANO AB, Karlshamn (SE)

(72) Inventor: Jens Schouenborg, Lund (SE)

(73) Assignee: NEURONANO AB

( * ) Notice: Subject to any disclaimer, the term of this patent is extended or adjusted under 35 U.S.C. 154(b) by 811 days.

(21) Appl. No.: 16/616,084

(22) PCT Filed: May 22, 2018

(86) PCT No.: PCT/SE2018/000013
§ 371 (c)(1),
(2) Date: Nov. 22, 2019

(87) PCT Pub. No.: WO2018/217147
PCT Pub. Date: Nov. 29, 2018

(65) Prior Publication Data
US 2020/0093512 A1     Mar. 26, 2020

(30) Foreign Application Priority Data
May 23, 2017    (SE) .................................. 1700104-1

(51) Int. Cl.
*A61B 5/00*   (2006.01)
*A61B 17/34*  (2006.01)
(Continued)

(52) U.S. Cl.
CPC ........ *A61B 17/3468* (2013.01); *A61B 5/0084* (2013.01); *A61B 5/01* (2013.01);
(Continued)

(58) Field of Classification Search
CPC .......... A61B 17/3468; A61B 2560/063; A61B 2562/0209; A61B 5/0084; A61B 5/01;
(Continued)

(56) References Cited

U.S. PATENT DOCUMENTS

| 6,080,160 A | 6/2000 | Chen et al. ..................... 606/72 |
| 2001/0025179 A1 | 9/2001 | Levine ............................ 606/45 |

(Continued)

FOREIGN PATENT DOCUMENTS

| WO | WO 2013/191612 A1 | 12/2013 |
| WO | WO 2014/179599 A1 | 11/2014 |
| WO | WO 2015/094076 A1 | 6/2015 |

OTHER PUBLICATIONS

International Search Report dated Aug. 14, 2018 in corresponding PCT International Application No. PCT/SE2018/000013.
(Continued)

*Primary Examiner* — George Manuel
(74) *Attorney, Agent, or Firm* — Ostrolenk Faber LLP

(57) ABSTRACT

A device selected from microelectrode, temperature sensor, optical sensor, optical fibre, temperature control element, and microdialysis probe for insertion into soft tissue comprises a body with a distal terminal section and a layer of an agent such as gelatin capable of forming a gel with aqueous body fluid on the terminal section. The terminal section and the gel-forming layer have a temperature of more than 30° C. below body temperature during a period of time prior and up to insertion. Also disclosed is method of insertion, an insertion assembly and a use of the device.

37 Claims, 6 Drawing Sheets

(51) Int. Cl.
  *A61B 5/01* (2006.01)
  *A61F 7/00* (2006.01)
  *A61F 7/02* (2006.01)
  *A61N 1/05* (2006.01)
  *A61B 5/24* (2021.01)

(52) U.S. Cl.
  CPC ............... *A61B 5/24* (2021.01); *A61F 7/007* (2013.01); *A61F 7/02* (2013.01); *A61N 1/0551* (2013.01); *A61F 2007/0075* (2013.01); *A61F 2007/0219* (2013.01)

(58) Field of Classification Search
  CPC ......... A61B 5/14528; A61B 5/24; A61B 5/25; A61B 5/293; A61F 2007/0075; A61F 2007/0095; A61F 2007/0219; A61F 7/00; A61F 7/007; A61F 7/02; A61N 1/0531; A61N 1/0551
  See application file for complete search history.

(56) References Cited

U.S. PATENT DOCUMENTS

| | | |
|---|---|---|
| 2003/0028224 A1 | 2/2003 | McVenes et al. ............... 607/36 |
| 2003/0078644 A1 | 4/2003 | Phan .............................. 607/119 |
| 2005/0090880 A1 | 4/2005 | Venturelli ........................ 607/99 |
| 2007/0073130 A1 | 3/2007 | Finch et al. .................... 600/372 |
| 2009/0062745 A1 | 3/2009 | Qiu ................................. 604/197 |
| 2010/0010550 A1 | 1/2010 | Ponomarev ....................... 607/3 |
| 2012/0296404 A1 | 11/2012 | Carpentier et al. ........... 607/116 |
| 2013/0072776 A1 | 3/2013 | Fujii et al. ..................... 600/378 |
| 2015/0151107 A1* | 6/2015 | Schouenborg ........... A61B 5/24 604/20 |
| 2017/0014858 A1 | 1/2017 | Takei et al. | |

OTHER PUBLICATIONS

Written Opinion dated Aug. 14, 2018 in corresponding PCT International Application No. PCT/SE2018/000013.

* cited by examiner

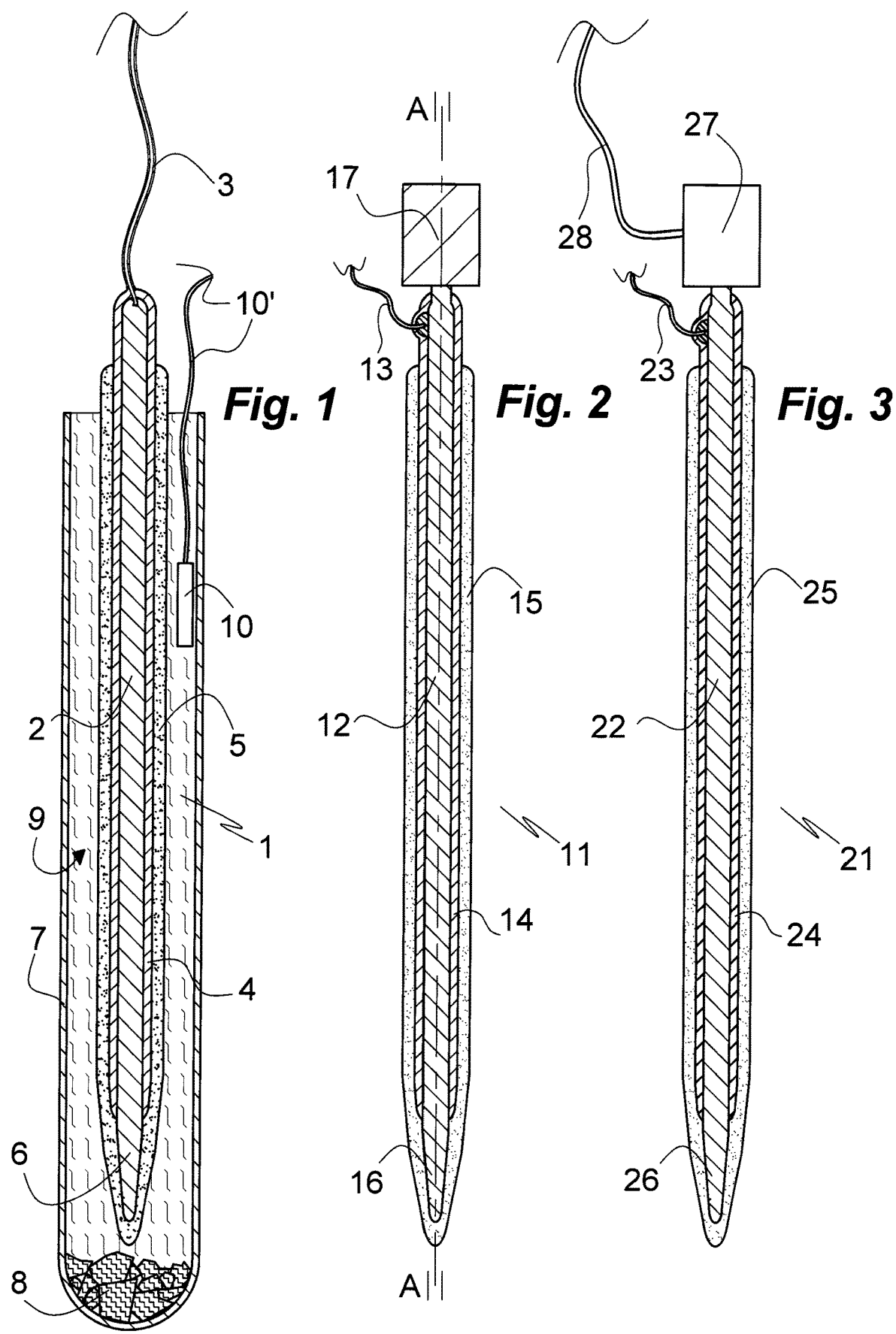

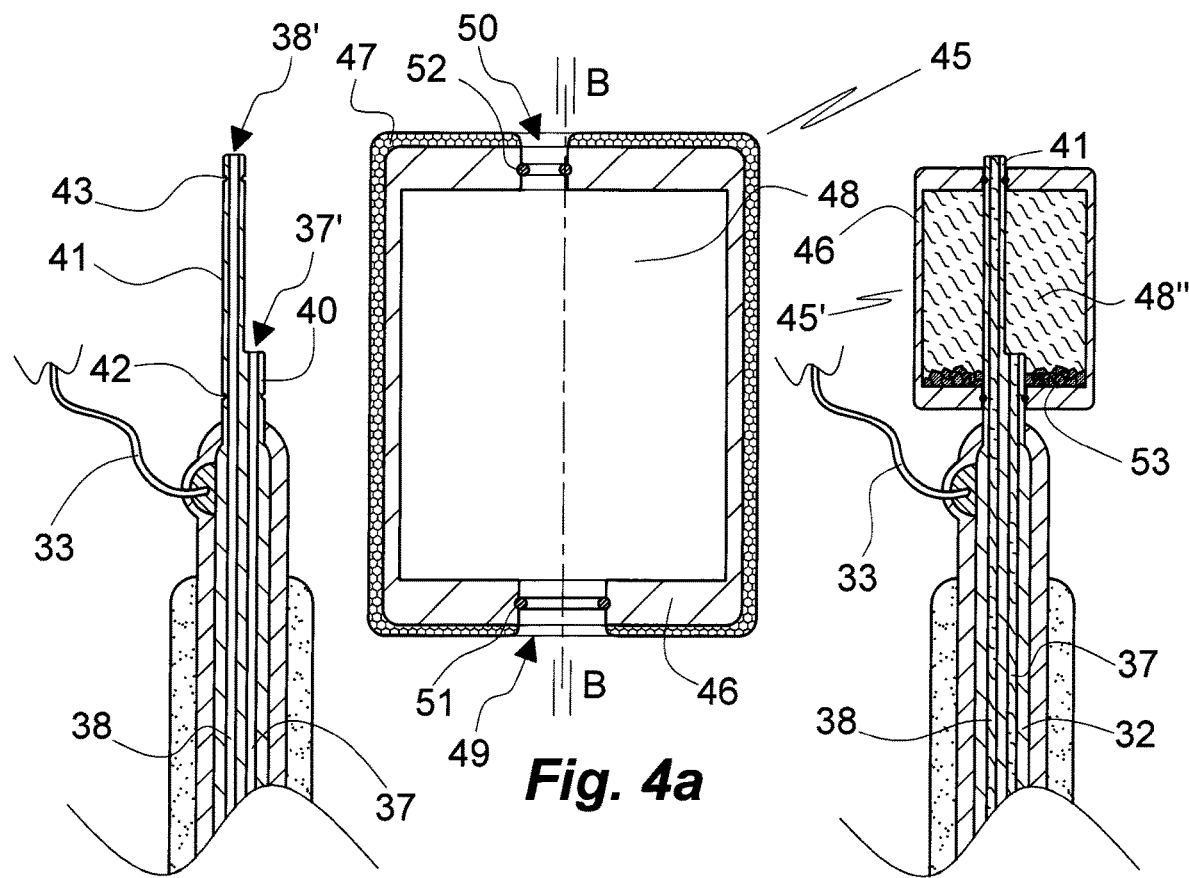
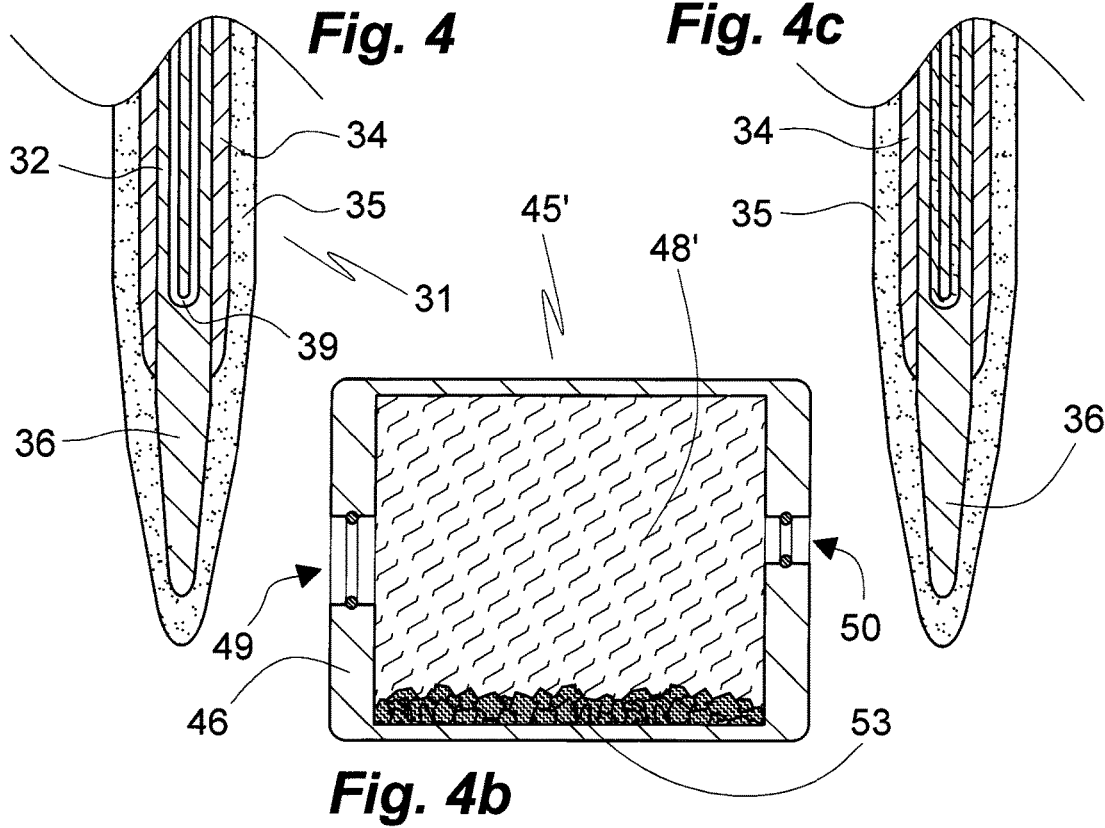

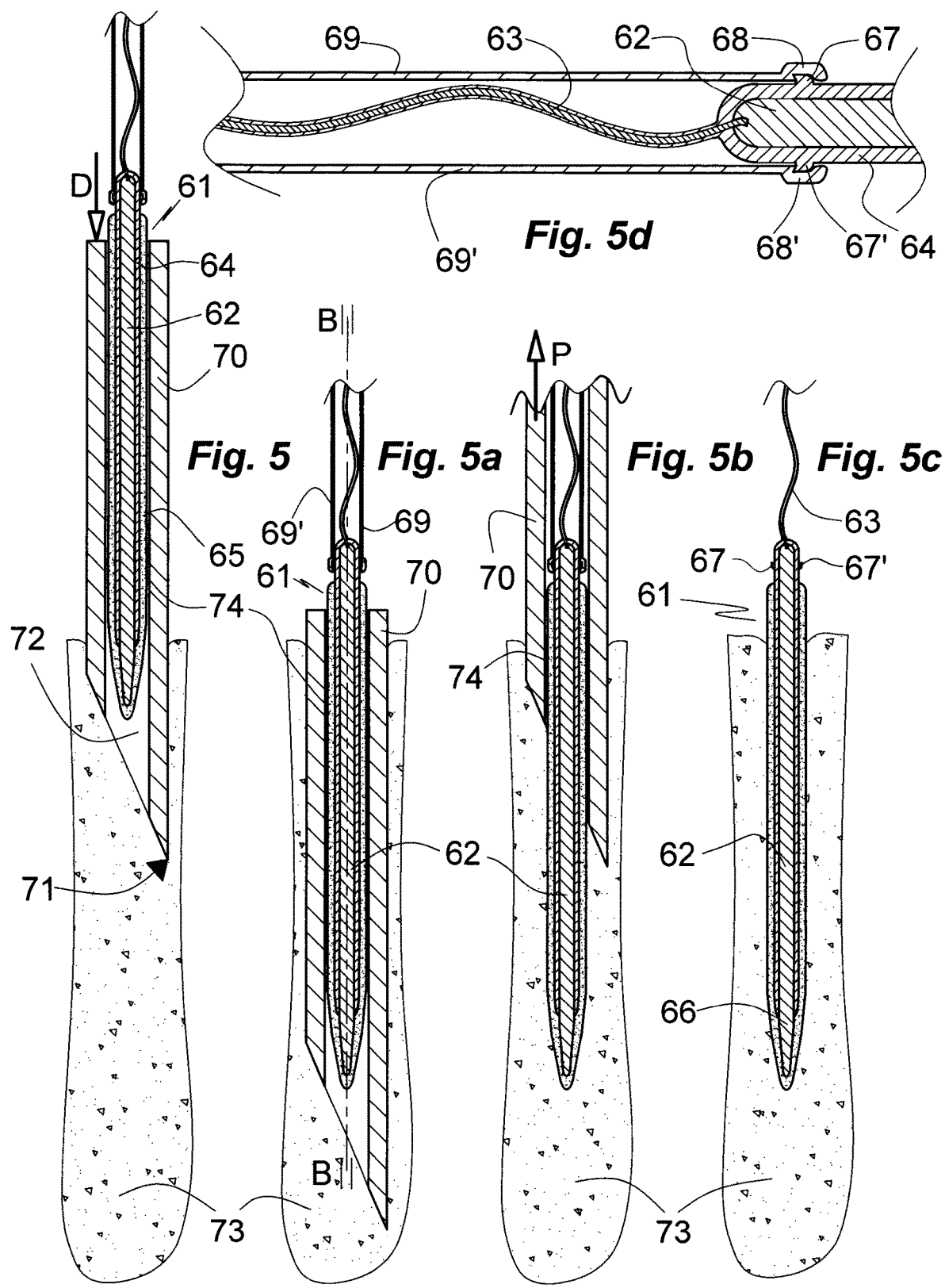

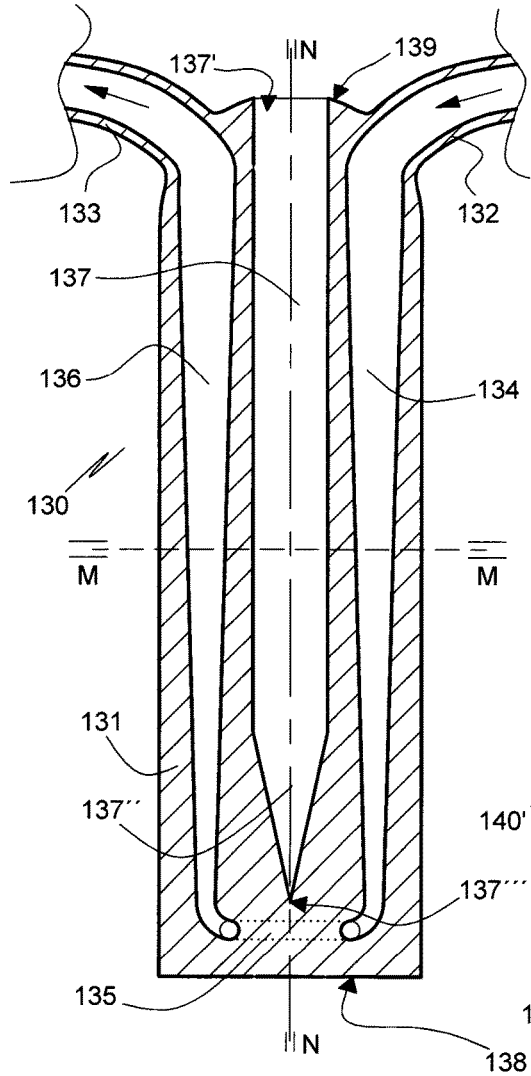
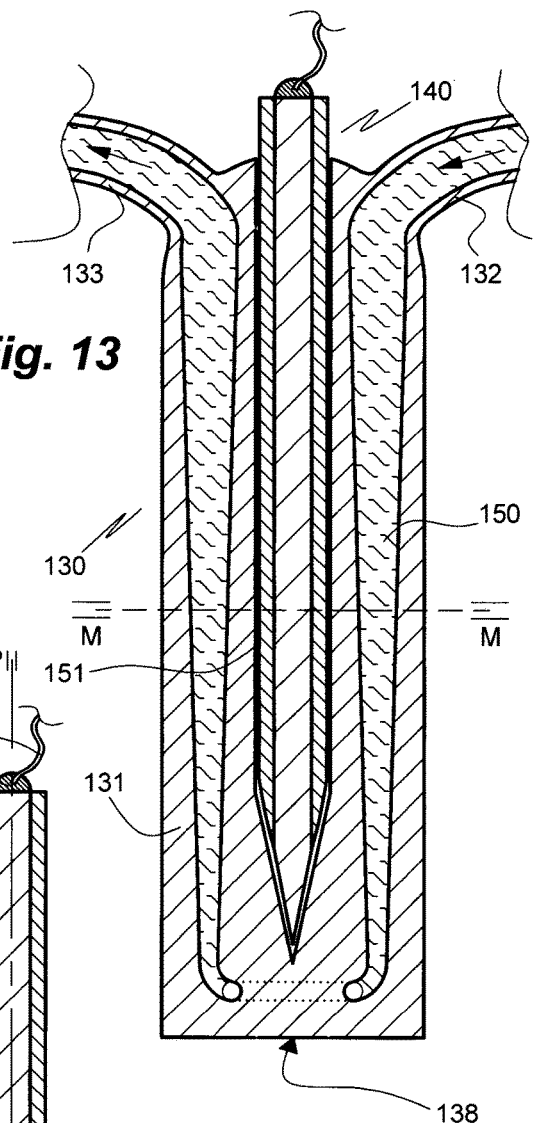
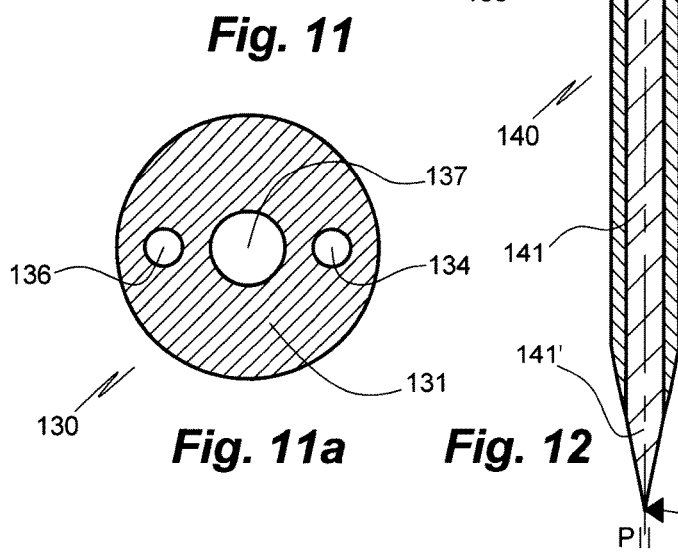
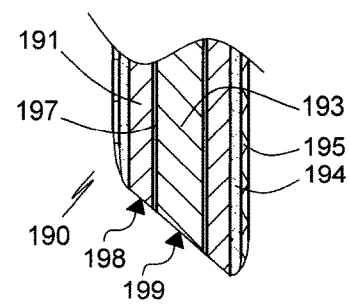

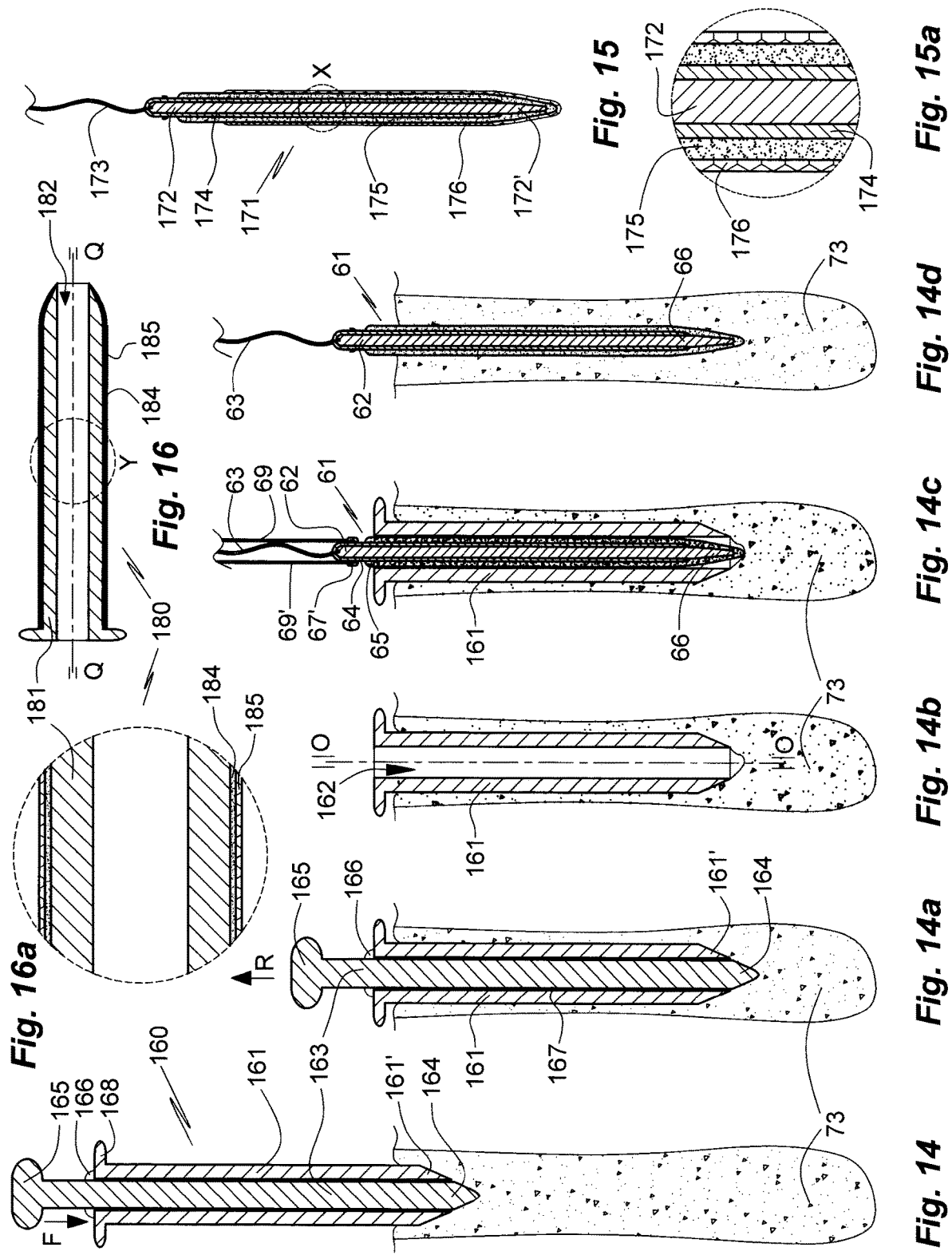

DEVICE FOR INSERTION INTO NERVOUS TISSUE

CROSS-REFERENCE TO RELATED APPLICATIONS

The present application is a 35 U.S.C. §§ 371 national phase conversion of PCT/SE2018/000013, filed May 22, 2018, which claims priority to Swedish Patent Application No. 1700104-1, filed May 23, 2017, the contents of which are incorporated herein by reference. The PCT International Application was published in the English language.

FIELD OF THE INVENTION

The present invention relates to a diagnostic and/or therapeutic device for insertion into soft tissue, in particular nervous or endocrinous tissue, to an insertion assembly comprising the device and insertion means, to methods of insertion of the device into nervous tissue, and to uses thereof. A preferred embodiment of the device is a microelectrode. Other embodiments of the device are temperature and optical sensors, optical fibres, temperature control elements, microdialysis probes, and the like.

BACKGROUND OF THE INVENTION

The insertion of microelectrodes or other devices into soft tissue, in particular nervous or endocrinous tissue, is accompanied by damage to the tissue. To ensure proper function of the electrode upon insertion prevention of excessive damage is of paramount importance. Various measures can be taken to minimize damage, such as a design of the microelectrode emphasizing reduction of electrode diameter and provision of a coat of a material of a low friction coefficient on the electrode. The friction reducing material may be permanent, such as an electrically insulating material covering most of the electrode body, or may be temporary, such as a material dissolving upon and even during insertion of the electrode. A problem with friction reducing materials designed to dissolve in body fluid during and upon insertion is to control their premature dissolution or detachment during insertion. A particularly friction reducing material is gelatin. Gelatin has the additional advantage of reducing cell damage when used as a temporary coat on a microelectrode.

OBJECTS OF THE INVENTION

An object of the invention is to provide a device of the aforementioned kind, in particular a microelectrode, coated with a friction reducing material dissolvable in body fluid upon insertion into soft tissue, in particular nervous or endocrine tissue, in a state in which dissolution is controlled, in particularly delayed, during and upon insertion.

Another object is to provide an assembly comprising a device of this kind, in particular a microelectrode, and a separate means for its insertion into the tissue.

An additional object of the invention is to provide bundles and arrays of such microelectrodes and arrays of such bundles.

Still another object of the invention is to provide a method of insertion of the device of the invention, in particular of a microelectrode, into nervous tissue by use of a separate insertion means.

Further objects of the invention will become apparent from the following summary of the invention, a number of preferred embodiments illustrated in a drawing, and the appended claims.

SUMMARY OF THE INVENTION

The present invention is based on the insight that dissolution of gels formed by contact of gel forming biocompatible agents, in particular gelatin, with aqueous body fluids in a warm-blooded person or animal can be delayed by lowering the temperature at the contact site.

In addition, the present invention is based on the insight that lowering the temperature of soft tissue in contact with a medical device being inserted into it protects the tissue from damage. According to the invention the temperature of the tissue contacted by a device being inserted to it is cooled by the device, which has a temperature substantially below tissue temperature, such as a temperature of 30° C. or more, in particular of 40° C. or more below tissue temperature.

Gel forming biocompatible agents are useful in the implantation of medical devices such as microelectrodes into soft tissue such as nervous or endocrine tissue. The gel forming agents are applied in form of single or multiple layers on the devices forming coats swelling in contact with aqueous body fluid and then dissolving in the fluid or dissolving in the fluid upon degradation. Insertion of medical devices coated in this manner into soft tissue, in particular nervous or endocrine tissue, protects the tissue from damage. A moderate reduction of the temperature at the implantation site by, for instance, 5° C. or 10° C. or 15° C. is often sufficient to substantially delay dissolution of the gel, such as by a time factor of 2 or more.

While gelatin from warm blooded animals swells quickly in contact with aqueous body fluid at body temperature and dissolves at body temperature when native, its dissolution is substantially reduced at a temperature of about 30° C. and below and/or by cross-linking it. Temperatures lower than 20° C. additionally delay dissolution.

Gelatin from cold blooded animals, in particular fish gelatin, dissolves already at lower temperature, such as at temperatures below the body temperature of warm blooded animals. This has to be taken into consideration when selecting gelatin for use in the invention. Also within the ambit of the invention is to use combinations of gelatin from different sources and cross-linked gelatin. The use of gelatin of a Bloom strength of below 300 is preferred.

Other preferred gel forming materials include hyaluronic acid in native and cross-linked form; whey protein, soy protein, casein; arabinoxylan; galactan; galactomannan; lichenan; xylan; cellulose derivatives such as hydroxymethylpropyl cellulose; chitosan; gum Arabic; carboxyvinyl polymer; sodium polyacrylate; carboxymethyl cellulose; sodium carboxymethyl cellulose; pullulan; polyvinylpyrrolidone; karaya gum; pectin; xanthane gum; tragacanth; alginic acid; chitin; poly-glycolic acid; poly-lactic acid; co-polymer of poly-glycolic and poly-lactic acid; co-polymer of poly-lactic acid and polyethylene oxide; polyethylene glycol; polydioxanone; polypropylene fumarate; poly(ethyl glutamate-co-glutamic acid); poly(tert-butyloxy carbonylmethyl glutamate); poly-caprolactone; poly(caprolactone-co-butylacrylate); poly-hydroxybutyrate and copolymers thereof; poly(D,L-lactide-co-caprolactone); poly(glycolide-co-caprolactone); poly(phosphate ester); poly(amino acid); poly(hydroxybutyrate); polydepsidpeptide; maleic anhydride copolymer; polyphosphazene; polyiminocarbonate; poly[(7.5% dimethyl-trimethylene carbonate)-co-(2.5% trimethlyene carbonate)]; polyethylene oxide; homopolymer of polyvinyl alcohol; hydroxymethyl methacrylate; hydroxyl- or amino-terminated polyethylene glycol; acrylate-based copolymer such as methacrylic acid, methacrylamide; heparan sulfate; RGD peptide; polyethylene oxide; chrondroitin sulfate; YIGSR peptides; keratan sulfate; VEGF biomimetic peptide; perlecan (heparan sulfate proteoglycan 2); Ile-Lys-Val-Ala-Val (IKVAV) containing laminin alpha-1 chain peptide; modified heparin; fragment of fibrin; and their combinations.

A layer or coat of gel forming biocompatible agent can contain one or more pharmacologically active agents. Preferred agents include albumin, heparin, neurotransmitters such as small molecule neurotransmitters (for example acetylcholine, dopamine, serotonin, histamin, norepinephrine and epinephrine), amino acids (for example GABA, glycine and glutamate), neuroactive peptides (for example bradykinin, substance P, neurotensin, endorphins, enkephalin, dynorphins, neuropeptide Y, somatostatin, cholecystokinin) and soluble gases (for example nitric oxide). Other preferred agents comprise coagulation factors such as factor VIII or functional derivatives thereof; combinations of factor IX, II, VII and X; factor IX; a combination of von Willebrand factor and factor VIII; factor VIIa or human fibrinogen. Further preferred pharmacologically active agents are those controlling vasoconstriction, such as drugs promoting production of NO, in particular glyceryl nitrate or functional derivatives thereof. In cases where there is a risk that local vasoconstriction may lead to a brain infarct due to clogging of the affected vessel a drug against trombocyte aggregation can be used, such as, for instance, klopidogrel, tiklopidine, acetylsalicylic acid, dipyramidol, iloprost, abciximab, eptifibatide, tirofiban.

A layer or coat of gel forming biocompatible agent or the outmost layer or coat of two or several layers can be covered by a dissolution retarding layer, in particular a lipid layer, such as one comprising or consisting of glyceryl-trilaureate, or a layer of polyvinyl alcohol/polyethylene glycol graft polymer or one of mucus.

The layer or coat of a material capable of forming a gel in contact with aqueous body can comprise two or more sub-layers differing in regard of their swelling and dissolution properties, in particular an inner layer capable of swelling and dissolving more readily than an outer layer.

According to a preferred aspect of the invention the layer or coat of gel forming agent can be provided with a coat of ice prior to insertion into the tissue. For providing a layer of ice the microelectrode has to be cooled substantially below 0° C., such as below −10° C. or −20° C. or even below −60° C. or −80° C., then to be dipped into cold water for a short time such as half a second or a second, and even for 5 seconds or 10 seconds or more, and withdrawn.

The present invention is furthermore based on the insight that the temperature reduction required for such delay in dissolution can be provided by means of the device to be implanted. Devices comprising or provided with agents capable of forming gels in contact with aqueous body fluid such as gelatin benefiting from a temperature reduction in their implantation comprise microelectrodes, temperature sensors, optical sensors, optical fibres, temperature control elements, microdialysis probes, and the like.

According to the invention is provided, as an exemplary embodiment of the device of the invention, a microelectrode for insertion into soft tissue, in particular nervous or endocrine tissue, comprising an oblong electrode body extending between a distal end and a proximal end, a first portion of an electrically insulating layer on a portion of the electrode body extending from the proximal end, and a layer of an agent forming a gel in contact with aqueous body fluid extending from the distal end of electrode body so as to cover at least a distal portion of the insulating layer, wherein the electrode body and the layers have an insertion temperature substantially below body temperature, in particular a temperature of more than 30° C., more preferred more than 40° C., below body temperature during a time period prior and up to insertion.

The microelectrode of the invention has a preferred width of up to 100 µm, in particular of up to 50 µm or up to 30 µm or up to 12 µm.

The length of the microelectrode of the invention is preferably adapted to the intended depth of insertion thereof.

The microelectrode of the invention can be a single microelectrode or one pertaining to a bundle or an array of microelectrodes and even to an array of bundles of microelectrodes. A bundle of microelectrodes comprises two or more microelectrodes attached to each other substantially in parallel in a permanent or temporary manner, wherein temporary manner means that a microelectrode is released from the attachment upon insertion into nervous or endocrine tissue, in particular upon contact with body fluid in the tissue.

The microelectrode body is preferably of a metal of good thermal and electrical conductivity such as gold, platinum, iridium, silver, copper, stainless steel, tungsten or comprises such metal or is an alloy thereof but may also be of an electrically conducting polymer or carbon or a combination thereof.

According to a preferred embodiment the proximal end of the microelectrode body is in thermal contact with a cooling source, such as a heat sink of a temperature substantially below body temperature, in particular a temperature of lower than 10° C., more preferred lower than 5° C., even more preferred lower than 0° C., and even lower than −10° C. or −20° C. According to a particular preferred embodiment the cooling source is or comprises a Peltier element.

According to a preferred embodiment of the invention a proximal portion of the device in a state immediately prior to insertion or later is at a lower temperature than a distal portion thereof so as to function as a heat sink for the distal portion, thereby delaying the warming thereof.

More generally the present invention is embodied by a device for insertion into soft tissue, in particular nervous or endocrine tissue, selected from microelectrode, temperature sensor, optical sensor, optical fibre, temperature control element, microdialysis probe, comprising:

a device body extending between a distal end and a proximal end comprising a distal terminal section extending from the distal end in a proximal direction;

optionally one or more layers of one or more electrically non-conducting materials that do not dissolve in or swell in contact with aqueous body fluid disposed on the distal terminal section or on portions thereof;

a layer of a material capable of forming a gel in contact with aqueous body fluid covering the distal terminal section;

wherein the distal terminal section, the one or more layers of one or more materials that do not dissolve in or swell in contact with aqueous body fluid and the layer of material capable of forming a gel in contact with aqueous body fluid have a temperature substantially below body temperature, in particular a temperature of more than 30° C., more preferred more than 40° C., below body temperature during a time period prior and up to insertion; and wherein the distal terminal section, the one or more layers of one or more materials that do not dissolve in or swell in contact with aqueous body fluid and the layer of material capable of forming a gel in contact with aqueous body fluid are optionally covered by a layer of ice.

The one or more layers of one or more materials that do not dissolve in or swell in contact with aqueous body fluid are preferably electrical insulators, that is, not electrically conducting.

According to a preferred aspect of the invention, in a state prior to insertion, the distal terminal section has a temperature comprised by range of from −7° C. to 3°, in particular from −3° C. to 1° C., even more preferred from −1° C. to 0° C., with the proviso that the distal section is not covered by a layer of ice.

According to another preferred aspect of the invention, in a state prior to insertion, the distal terminal section has a temperature comprised by the range of from −20° C. to 0° C., such as from −7 to 0° C., in particular from −3° C. to 0° C., even more preferred from −1° C. to 0° C., with the proviso that the distal terminal section is covered by a layer of ice.

It is preferred for the temperature of the distal terminal section to increase in a radial direction.

It is also preferred for the temperature of the device to decrease from the distal terminal section in a proximal direction, in particular within a range of up to 2° C. or up to 5° C. or more.

According to a preferred aspect of the invention the device is a microelectrode and its body is or comprises electrically conducting material; wherein said one or more layers of one or more materials that do not dissolve in or swell in contact with aqueous body fluid are of or comprise an electrically insulating material. The microelectrode preferably comprises a cooling means, such as a heat sink, in particular one of a metal or a metal alloy of high specific weight such as copper, iron, steel, lead, chromium, nickel, silver, gold, and their alloys. It is preferred for the cooling means to be mounted at a proximal portion of the electrode body and to be in thermally conducting contact with it. It is preferred for the cooling means to be or comprise a Peltier element, preferably one that is mountable on the electrode and dismountable from it. It is also preferred for the cooling means to comprise a container, in particular a closed container, having a void at least partially filled with a coolant at low temperature, in particular dry ice. In a preferred embodiment with dry ice as coolant the container void is in communication with one end of a channel disposed in the electrode body or the layer of material capable of forming a gel in contact with aqueous body fluid, the other end of the channel opening into the environment. The container is preferably mountable on the electrode and dismountable from it.

A microelectrode of the present invention can be comprised by a microelectrode bundle or array.

Also disclosed are devices of the invention in form of:
Optical sensor having a body constituted by or comprising a detector of UV, visible or IR radiation constituting or comprised by said terminal section;
Temperature sensor having a body constituted by or comprising a thermocouple; an optical fibre having a body constituted by or comprising a distal terminal portion of the optical fibre;
Temperature control element constituted by or comprising a device body in form of an oblong metallic rod optionally further comprising a heat sink, a Peltier element and/or a container filled with coolant such as dry ice mounted at its distal end in a thermally conductive manner;
Microdialysis probe constituted by or comprising a device body having an aqueous fluid conduit provided with a semi-permeable membrane.

Any combination comprising two or more devices of the invention is within the ambit of the invention such as, for instance, the combination of a microelectrode and an optical fibre.

Also disclosed is an assembly for insertion of the device of the invention into soft tissue comprising the device and a cooling means separate of the device comprising a surgical cannula or needle having a lumen wherein the device is disposable. Prior to insertion of the device into soft tissue the cannula comprising the device is of a temperature substantially below body temperature, such as a temperature of 30° C. or 40° C. or more below body temperature.

According to the invention is also disclosed an apparatus for cooling a device of the invention, in particular a microelectrode, comprising a wall, a lower end and an upper end, a channel extending from the upper end towards the lower end and having an open upper end and a diameter adapted to receive the device by insertion with its distal end foremost, the apparatus comprising a conduit with open ends for a cooling fluid and designed for controlling the temperature of the wall in a manner to make it decrease from its lower end towards its upper end.

It is preferred for the conduit to extend from an upper portion to a lower portion thereof and/or to narrow towards the lower end. The mass of the apparatus wall preferably increases towards the lower end. The cooling fluid is preferably a liquid such as ethanol or glycol that does not solidify at temperatures above −5° C., in particular at temperatures above −10° C. or −20° C.

Additionally disclosed is a method of inserting the device of the invention into soft tissue, in particular nervous or endocrine tissue, comprising:
Providing a surgical cannula or needle having a lumen;
Disposing the device in the lumen with its distal end facing the distal opening of the cannula;
Cooling the cannula to a temperature substantially below body temperature, such as a temperature of 30° C. or 40° C. below body temperature for a time sufficient to bring it to that temperature;
Inserting the cooled cannula into the tissue to a desired depth;
Expelling the device from the distal opening of the cannula then withdrawing the cannula or withdrawing the cannula while keeping the device at the desired position.

According to a preferred embodiment of the invention a surgical cannula or needle for insertion of a device of the invention into soft tissue is covered by a layer of an agent capable of forming a gel on contact with aqueous body fluid, in particular native or modified gelatin. Optionally the layer of gel-forming agent is covered by a layer of ice. The layer of ice can be applied immediately prior to insertion but also well in advance to insertion, in which case the ice-covered device is stored at a low temperature, such as at a temperature of −10° or less, in particular at a temperature of about −20° or less, and is allowed to warm up to a desired temperature immediately prior to insertion, such as to a temperature of about 0° C.

Furthermore, according to the invention, a method of inserting the device of the invention into soft tissue, in particular nervous or endocrine tissue, comprises:

Providing a channel in the tissue filled with an aqueous gel of a biocompatible material, in particular gelatin;

Inserting the device into the channel, for instance by means of a syringe.

The device or assembly of the invention can be used for insertion of the device into soft tissue, in particular nervous or endocrine tissue, or into a channel in such tissue filled with an aqueous gel of a biocompatible agent, in particular gelatin.

According to a still further preferred aspect of the invention is disclosed a combination of surgical cannula or needle and cannula or needle channel insert for inserting a device of the invention into soft tissue, comprising co-operating means capable of stopping the distal displacement of the insert in the cannel so as to provide the combination with a joint distal needle point or tip having a co-planar or a co-curved face formed by distal face sections of the cannula and the insert. The join needle point is asymmetric or symmetric. It is preferred for a distal portion of the needle, in particular a portion extending in a proximal direction from the distal end, to be covered with an agent capable of forming a gel on contact with aqueous body fluid, the entire needle or the distal portion of the needle covered with agent capable of forming a gel optionally being covered by a layer of ice.

According a method of the invention for implantation of a medical device such as a microelectrode into soft tissue, in particular nervous or endocrine tissue, comprises:

Providing a surgical cannula or needle comprising a channel and an insert disposed in the channel, the insert comprising a means for stopping further distal displacement upon formation of a joint distal point with the needle;

Inserting the needle with the insert into soft tissue in a state of joint distal point formation;

Withdrawing the insert from the needle;

Inserting the medical device into the channel of the needle;

Withdrawing the needle from the tissue.

The invention will now be described in greater detail by reference to a number of preferred embodiments illustrated in a drawing, which is not to scale but only intended to illustrate the invention in principle.

SHORT DESCRIPTION OF THE FIGURES

FIG. 1 is a first embodiment of the device of the invention in form of a microelectrode shown in an axial section (corresponding to section A-A in FIG. 2) disposed in a cooling environment;

FIG. 2 is a second embodiment of the device of the invention in form of a microelectrode shown in an axial section A-A;

FIG. 3 is a third embodiment of the device of the invention in form of a microelectrode shown in an axial section corresponding to section A-A in FIG. 2;

FIG. 4 is a fourth embodiment of the device of the invention in form of a microelectrode shown in an axial section;

FIG. 4a is a coolant container mountable at the microelectrode of FIG. 4 in an axial section B-B;

FIG. 4b shows the container of FIG. 4a loaded with coolant, in the same section but horizontally disposed;

FIG. 4c shows the coolant loaded container of FIG. 4b mounted on the microelectrode of FIG. 4;

FIGS. 5-5c show a fifth embodiment of the device of the invention in form of a microelectrode disposed in the lumen of a cold needle for its insertion into soft tissue, in an axial section B-B; at an intermediate stage of needle insertion (FIG. 5); upon full insertion of the needle (FIG. 5a); at an intermediate stage of needle withdrawal (FIG. 5b); upon full withdrawal of the needle (FIG. 5c);

FIG. 5d is an enlarged sectional view of the distal terminal portion of the microelectrode with a releasable plunger attached at its proximal end in the state of FIGS. 5-5b;

FIGS. 11, 11a and 13 show an apparatus for cooling the device of the invention in form of a microelectrode, in axial sections and in radial section, respectively;

FIG. 12 shows, in axial section, a microelectrode dimensionally adapted for insertion in a central channel in the apparatus of FIGS. 11, 11a, 13;

FIGS. 14, 14a show the combination of a surgical needle and a cylindrical insert disposed in the channel of the needle at the start of and upon insertion into soft tissue, in an axial section;

FIG. 14b shows the insert inserted in the tissue upon withdrawal of the needle, in the same section;

FIG. 14c shows a microelectrode inserted into the channel of the insert disposed in the tissue, in the same section;

FIG. 14d shows the microelectrode disposed in the tissue upon withdrawal of the insert, in the same section;

FIGS. 15, 15a show a variety of the microelectrode of FIGS. 5-5d, in the same section;

FIGS. 16, 16a show a variety of the insert of FIGS. 14-14c, in the same section;

FIG. 17 shows a distal terminal portion of a variety of the combination of surgical needle 161 and cylindrical insert 163 of FIGS. 14, 14a, in the same section.

DESCRIPTION OF PREFERRED EMBODIMENTS

Example 1

Figure 6:
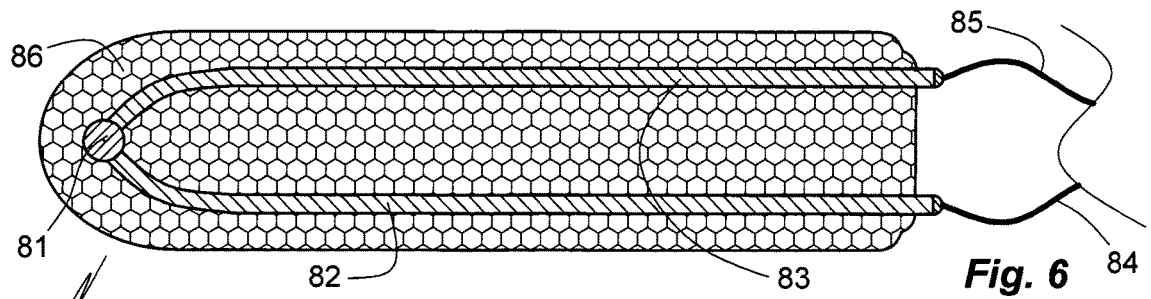
FIG. 6 shows a sixth embodiment of the device of the invention in form of a temperature sensor, in an axial section.

FIG. 1 illustrates a microelectrode of the art 1 comprising an oblong cylindrical metallic electrode body 2, for instance of silver, gold, platinum or iridium, with a narrowing distal tip 6 and a flexible electrical lead 3 attached to its distal end. Except for the tip 6 the electrode body 2 is electrically insulated by a layer 4 of a polymer material such as polyurethane or Parylene C. Except for a portion extending from the proximal end the electrode body 2 and the tip 6 is covered with a layer 5 of dry gelatin of a Bloom strength of 120. The electrode 1 is shown inserted in a cooling vessel 7 of the shape of a test tube with its distal tip 6 foremost. The vessel 7, which may be thermally insulated (not shown) is loaded with dry ice 8 disposed at the bottom thereof. The electrode 1 is cooled by gaseous carbon dioxide 9 evaporated from the dry ice 8. The temperature of the carbon dioxide 9 atmosphere in the vessel is monitored by a thermocouple 10; alternatively or additionally the temperature of the electrode 1 can be monitored by a thermocouple 10 attached to or incorporated into the electrode 1. By a flexible conductor 10' the thermocouple 10 is connected to a display unit (not shown) at which the measured temperature can be read. The time required for the thermocouple 10 to reach a desired low temperature when inserted into the cooling vessel 7 can be easily determined experimentally. Upon reaching that temperature the microelectrode 1 is withdrawn from the vessel 7 and inserted into nervous tissue without delay, so as having substantially the same temperature at the onset of insertion as its temperature at withdrawal from the vessel 7, for instance at temperature of $-10°$ C. or $-20°$ C. Upon insertion of the cold microelectrode into soft tissue the uptake of water from surrounding body fluid is delayed by the low temperature. This allows the microelectrode to be more precisely disposed in the nervous tissue in respect of a target thereof, in particular of a neuron or a group of neurons, prior to the swelling and dissolution of the gelatin layer 7. Other biocompatible materials capable of swelling such as alginate can be incorporated into the layer 7 or constitute it.

A signal from the microelectrode can alternatively be transmitted wireless to an extracorporeal display unit by an implanted microwave transmitter or electromagnetic inductor.

Example 2

The design of the microelectrode of the invention 11 shown in FIG. 2 in an axial section A-A substantially corresponds to that of the microelectrode 1 of Example 1 except for a cooling means in form of heat sink 17 attached to the electrode body 12 at its proximal end in a thermally communicating manner. Prior to implantation of the microelectrode 11 the heat sink 17 is cooled in combination with the electrode 11 or separately to a low temperature, such as the temperature to which the electrode 11 is cooled or to an even lower temperature or substantially lower temperature. With the heat sink 17 at a lower temperature than the electrode 11 heat flows from the electrode body 12 to the heat sink 17 thereby cooling the electrode 11 and thus, when being contacted by body fluid, delaying swelling and dissolution of the gelatinous or other swellable layer 15 on an insulating layer 14 covering most of the electrode body 12. Suitable heat sink materials comprise steel, copper, chromium, and phenol formaldehyde polymer. The electrode body 12 is electrically connected with a power source (not shown) and/or an instrument for detecting voltage variations (not shown) by means of an insulated flexible lead 13. The procedure for insertion essentially corresponds to that of the device 1 of FIG. 1. Cooling of the microelectrode 11 with its heat sink 17 prior to insertion into soft tissue can be carried out in the same manner as described in Example 1 for the microelectrode 1 but it is also possible to cool the heat sink 17 separately. In such case, the heat sink 17 can have the form of a container, in particular of a thermally insulated container, comprising a lock through which the container can be loaded with a cooling medium such as dry ice and even liquid nitrogen, and then closed.

Example 3

The design of the microelectrode of the invention 21 shown in FIG. 3 in an axial section corresponding to axial section A-A of the embodiment of FIG. 2 substantially corresponds to that of the microelectrode 11 of Example 2 except for a cooling means in form of a Peltier element 27 being attached to the electrode body 22 at its proximal end in a thermally communicating manner instead of a heat sink. The Peltier element 27 is energized via an insulated flexible electric lead 28. The microelectrode 21 comprises correspondingly disposed insulating and swellable layers 24, 25 on the electrode body 22, the narrowing distal terminal portion 26 of which is similarly free of insulation 24. The electrode body 22 is electrically connected with a power source (not shown) and/or an instrument for detecting voltage variations (not shown) by means of an electrically insulated flexible lead 23. Upon completion of the insertion procedure the cooled tissue can be brought to body temperature by switching the Peltier element 27 to a warming mode to promote dissolution of the now swollen swellable layer 25.

Example 4

Except for the cooling means and the distal terminal portion 40, 41 the design of the microelectrode of the invention 31 shown in FIG. 4 in an axial section corresponding to axial section A-A of the embodiment of FIG. 2 substantially corresponds to that of the microelectrode 11 of Example 2. On its oblong electrode body 32 the microelectrode 31 comprises correspondingly disposed electrically insulating and swellable layers 34, 35. Similarly the narrowing distal terminal portion 36 of the electrode body 32 is similarly free of insulation 34. By means of an electrically insulated flexible lead 33 the electrode body 32 is electrically connected with a power source (not shown) and/or an instrument for detecting voltage variations (not shown).

The cooling means comprises a separate dry ice container 45 shown in FIG. 4a, which can be mounted at the distal terminal portion 40, 41 of the electrode 31 in the following manner. The dry ice container 45 of cylindrical form comprises aligned bottom and top openings 49, 50. The proximal terminal section 41, 42 is insertable with its proximal end foremost into the bottom opening 49 of the container 45. Displacing the partially inserted terminal section 41, 42 further towards the top opening 50 in a manner aligning the terminal section 41 with the top opening 50 allows the proximal end of terminal portion 41 to be inserted into the top opening 50, then to make it protrude from it by a short distance. The displacement comes to an end by circumferential grooves 42, 43 in sections 40 and 41 engaging with annular rubber seals 51, 52 disposed in grooves provided in the cylindrical walls of openings 49, 50. The axial distance between the seals 51, 52 correspond to that of grooves 42, 43. The container 46 is preferably of a metal such as steel or aluminium, or of reinforced polymer. The container 45 is preferably thermally insulated; this is only shown in FIG. 4a.

Prior to use the container 45 is disposed about horizontally in respect of it central axis B-B and loaded with dry ice 53 through one of its openings, preferably the larger bottom opening 49, to form the loaded container 45' shown in FIG. 4b. In the same disposition the proximal terminal portions 40, 41 of the microelectrode's body 32 are inserted through the bottom opening 49 and, after further displacement in the same direction, the proximal terminal portion 41 is inserted into the top opening and secured in this disposition by the rubber rings 51, 52 sealingly locking with the grooves 42, 43. Thereby an axially extending first channel 37 in the electrode body 32 is put into communication with the sealed interior space 48" of the container 45 filled with gaseous carbon dioxide evaporated from the dry ice 53. A second axially extending channel 38 disposed in parallel with the first channel 37 and in communication with it at their distal ends by a hemicircular channel bridge 39. The pressure building up in the sealed interior space 48" of the container 45 forces cold carbon dioxide into the first channel 37 through the opening 37' thereof, the carbon dioxide then consecutively passing through the first channel 37, the channel bridge 39 and the second channel 38, which it leaves at the open end 38' thereof passing into the atmosphere. On its way through the channels 37, 38 and the channel bridge 39 the carbon dioxide cools the electrode body 32 and so delays the swelling of the swellable gelatin layer 35.

Example 5

FIGS. 5-5c illustrate a microelectrode 61 corresponding to that of FIG. 1 except for comprising a circumferentially extending ridge 67, 67' for coupling of distal gripping claws 68, 68' of insertion plunger arms 69, 69' for displacement of the microelectrode 61 in a distal direction. The microelectrode 61 comprises an oblong cylindrical metallic electrode body 62, for instance of silver, gold, platinum or other noble metal or noble metal alloy, with a narrowing distal tip 66 and a flexible electrical lead 63 attached at its distal end. Except for the tip 66 the electrode body 62 is electrically insulated by a layer 64 of a polymer material such as polyurethane or Parylene C. Except for a portion extending from the proximal end the electrode body 62 and the tip 66 is covered with a layer 65 of dry gelatin. In FIG. 5 the microelectrode 61 is shown nearly fully disposed in the channel 72 of a needle 70 for injection. Prior to insertion the needle 70 and the microelectrode 61 are cooled to a low temperature, for instance 0° C., in the disposition shown in FIG. 5. Only a short proximal terminal portion of the microelectrode 61 provided with the gripping ridge 67, 67' and a flexible insulated lead 63 extends from the proximal lumen opening. The lead 63 provides electrical communication with, for instance, a control unit (not shown). The slanting distal end face of the needle 70 ends in a sharp tip 71. The outer diameter of the cylindrical microelectrode 61 (axis B-B, FIG. 5a) is somewhat smaller than the diameter of the channel 72. This allows the microelectrode 61 to be displaced in a distal or proximal direction in the channel 72 without meeting noticeable resistance. Resistance against displacement substantially increases once the microelectrode 61 is pushed out of the distal needle into soft tissue 73 (not shown). The design of the co-operating ridge 67 and the claws 68, 68' of the plunger 69, 69' allows considerable pressure to be exerted on the microelectrode 61 as far as the claws 68, 68' gripping the ridge 67 are disposed within the lumen 72; their radial displacement is limited by abutment against the wall of the channel 72.

After reaching a desired depth of needle 70 insertion the microelectrode 61 is kept in place by the plunger 69, 69' while the needle 70 is withdrawn in a proximal direction (FIG. 5b). It is important for the interstice 77 between the microelectrode 61 and the wall of the lumen 72 to be sufficiently wide to provide for easy pressure equilibration during withdrawal of the needle 70. The microelectrode is inserted into soft tissue at a temperature substantially below body temperature, thereby delaying dissolution of its gelatin layer 65. Upon full withdrawal of the needle 70 the claws 68, 68' of the plunger 69, 69 are easily released from the ridge 67, 67', leaving the microelectrode 61 in the desired inserted position (FIG. 5c). FIG. 5d is an enlarged view of the proximal terminal section of the microelectrode 61.

To increase its cooling capacity the needle 70 can be provided, at its proximal end, with a heat sink (not shown) like the heat sink 17 of Example 2 or with a Peltier element (not shown) like the Peltier element 27 of Example 3.

Example 6

The temperature sensor 80 illustrated in FIG. 6 comprises a thermocouple consisting of two dissimilar rigid insulated conductors 82, 83 joined by a solder point 81 at their distal ends. The conductors 82, 83 extend from the solder point 81 about parallel in a proximal direction and connected at their proximal ends with insulated electrical leads 84, 85 to an extracorporeal display (not shown) where the temperature at the solder point 81 can be read. The thermocouple 81, 82, 83 is embedded in a cylindrical matrix 86 of dry gelatin. The device 80 can be inserted into soft tissue by means of a surgical syringe in which it is disposed prior to insertion and cooled. Alternatively, a signal from the temperature sensor can be transmitted wireless to an extracorporeal display unit by an implanted microwave transmitter or electromagnetic inductor.

Example 7

Figure 7:
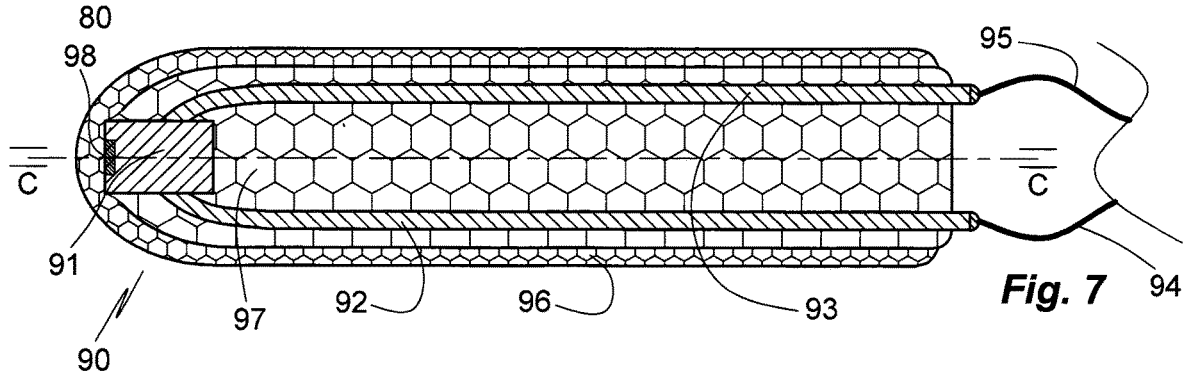
FIG. 7 shows a seventh embodiment of the device of the invention in form of an optical sensor, in an axial section.

The optical sensor 90 illustrated in FIG. 7 comprises a sensor unit 91 with a photodiode 98 or a phototransistor 98 disposed at its distal face. The electrical signal elicited by UV, visible or infrared light is conducted by insulated rigid conductors 92, 93 extending parallel in a proximal direction connected at their distal ends with flexible insulated leads 94, 95 providing electrical communication with an extracorporeal display unit (not shown). The sensor unit 91 and the rigid conductors 92, 93 are embedded in a first cylindrical matrix 97 of dry gelatin covered by a second matrix of dry gelatin 96, which matrixes are of a different physical nature. The matrices 96, 97 differ by the inner, first matrix 97 being of crosslinked gelatin and the outer, second matrix 96 being of non-crosslinked gelatin. The second matrix 96 is less resistant to dissolution than the first matrix 97, the swelling ad dissolution of which is thus delayed. The device 90 can be inserted into soft tissue by means of a surgical syringe in which it is disposed prior to insertion and cooled. The central axis C-C for the substantially cylindrical device is representative for the likewise substantially cylindrical devices of Examples 6 and 8-10.

Alternatively, a signal from the optical sensor can be transmitted wireless to an extracorporeal display unit by an implanted microwave transmitter or electromagnetic inductor.

Example 8

Figure 8:
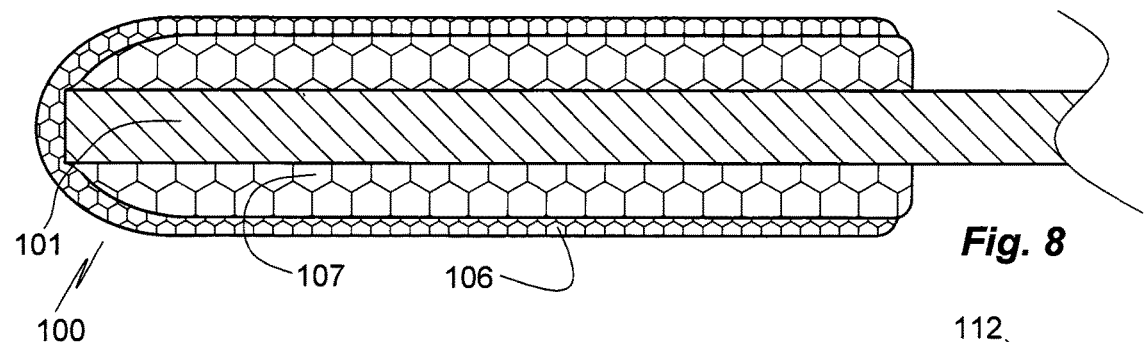
FIG. 8 shows a eight embodiment of the device of the invention in form of a optical fibre, in an axial section.

The optical fibre 100 illustrated in FIG. 8 forms the backbone of the device of the invention. It is covered by two layers 106, 107 the same manner as the optical sensor of Example 7, the outer layer 107 again being of non-crosslinked gelatin and the inner layer 106 of crosslinked gelatin. The device of the invention in form of the optical fibre 100 is defined by the distal terminal portion of the fibre 100 covered with gelatin 107, 106. The non-covered proximal portion of the fibre 100 provides optical connection with an optical detector or a light source (not shown) disposed at its other, extracorporeal end. The light source can alternatively be implanted in the tissue except for in the tissue volume to be targeted by the light emitted from the optical fibre.

Example 9

Figure 9:
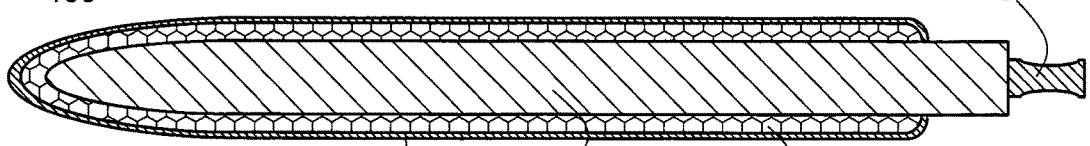
FIG. 9 shows a ninth embodiment of the device of the invention in form of a tissue temperature control element, in an axial section.

The tissue temperature control element 110 illustrated in FIG. 9 comprises an oblong cylindrical metallic core 111 narrowing towards its distal end. Except for a short terminal proximal portion the metallic core 111 is covered by a layer of cross-linked gelatin 116. A holding or mounting element 112 extends from its distal end; it can be used for holding the temperature control element 110 or for mounting a heat sink or Peltier element or the like. The gelatin layer 116 can be optionally covered by a layer 119 of a material protecting the gelatin layer 116 from contact with aqueous body fluid during insertion into soft tissue, such as a triglyceride layer of a melting point slightly above body temperature. The tissue temperature control element 110 can be disposed in the lumen of a surgical syringe, cooled in this disposition to a desired temperature, then injected into soft tissue at that temperature. Alternatively, the tissue temperature control element 110 can be temperature-adjusted by means of the apparatus for device temperature adjustment of EXAMPLE 12.

Example 10

Figure 10:
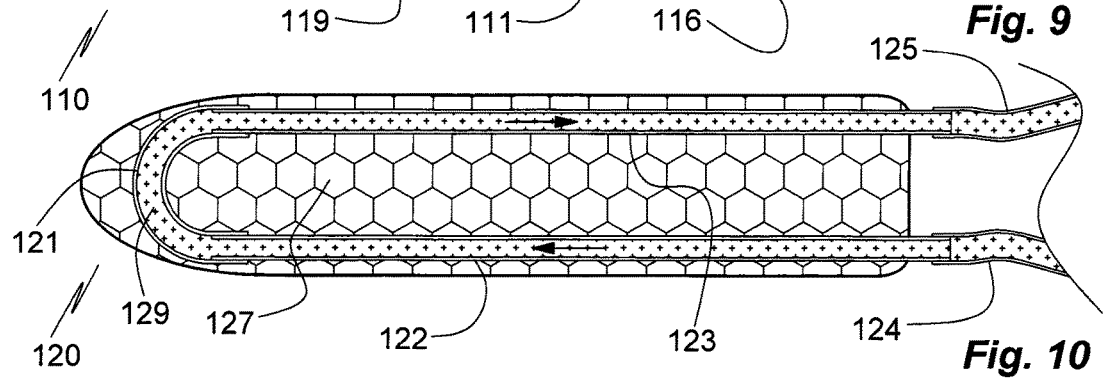
FIG. 10 shows a tenth embodiment of the device of the invention in form of a microdialysis probe.

The microdialysis probe 120 illustrated in FIG. 10 comprises a tubiform semipermeable membrane 121 in a hemicircular disposition at the distal end of the probe 120, connected at its ends to parallel, axially extending metallic or non-permeable polymer conductors 122, 123 which, at their proximal ends, are joined to flexible polymer tubes 124, 125. The membrane 121 and the polymer conductors 122, 123 are embedded in a matrix 127 of dry gelatin so to form the microdialysis probe 120 of cylindrical form and with a blunt distal end. The microdialysis probe 120 can be disposed in the lumen of a surgical cannula or needle (not shown) with its blunt end foremost, cooled to a desired temperature, then inserted by means of the cannula into soft tissue, followed by ejection from the cannula, which is withdrawn. Upon gelling of the gelatin matrix 127 an aqueous fluid 129, such as a Ringer solution, can be made to flow through the conduit formed by elements 124, 122, 121, 123, 125 in the direction indicated by arrow. When passing through the semipermeable membrane section 121 agents passing through the membrane from surrounding body fluid are washed out by the aqueous fluid 129, which can be collected and analysed. The fluid 129 can be fed to the device in a cooled state thereby controlling the dissolution of the layer of gel formed around the device.

Example 11

A layer or coat an agent capable of forming an aqueous gel ("gel forming agent") such as dry gelatin, disposed on a device of the invention, here exemplified by a microelectrode, is provided immediately prior to insertion into soft tissue with a coat of ice. Alternatively, the device of the invention is first cooled to a temperature substantially below 0° C., in particular to a temperature of –10° C. or –20° C. or even lower. The cooled microelectrode is then dipped for a short time into cold water of a temperature of about 0° C. time such for half a second or a second or up to 10 seconds or up to 20 seconds, then withdrawn and inserted immediately into the tissue; to prevent formation of larger ice crystals during immersion the immersed electrodes is displaced vertically up and down, in particular over a short distance. To provide a thicker layer of ice on the electrode the process can be repeated. The water into which the microelectrode is dipped preferably contains pieces of ice for temperature stabilization. The thickness of the ice layer is primarily controlled by the temperature of the electrode including the gel coat prior to immersion; at a constant immersion period a lower temperature of the microelectrode coated with gel forming agent prior to immersion will provide a thicker layer of ice. Shortening of the immersion period of a microelectrode coated with gel forming agent at a given low temperature will increase the radial temperature gradient in a peripheral direction, that is, from a central portion of the electrode at a lower temperature to a peripheral portion of the coat of gel forming agent at a higher temperature, with the proviso that the temperature of a peripheral portion of the coat of gel forming agent will be at 0° C. or lower until the ice layer on it has melted.

Alternatively, the device of the invention is cooled to a temperature substantially below 0° C. well before insertion, such as several hours or a day or several days or more prior to insertion, optionally provided with a layer of ice on the layer of gel forming agent, and stored at a temperature substantially below zero, such as freezer temperature of about –18° C. Prior to insertion into soft tissue the device is allowed to warm to a temperature of about 0° C. after having been provided with a layer of ice in the event of having been stored without such a layer.

Example 12

FIGS. 11, 11a and 13 illustrate an apparatus 130 for cooling the device of the invention in form of a microelectrode 140 in a manner so as to provide it with a temperature gradient increasing from its proximal end 140' towards its distal end 140". The apparatus 130 has the general form of a cylinder with a central axis N-N. The apparatus 130 has a wall 131 extending between its lower end 138 and its upper end 139. The apparatus 130 comprises a central cylindrical bore or channel 137 extending from the upper end 139 towards the lower end 138; the upper end 137' of the bore 137 is open; near its lower end the bore 137 comprises a converging section 137" ending in a point 137'''. The bore 137 has a diameter designed to receive the microelectrode 140 by insertion with its pointed distal end 140" foremost. The bore 137 has a diameter that is slightly larger than the diameter of the cylindrical microelectrode 140. The microelectrode 140 is designed to snugly fit into the bore 137, thereby providing for thermal contact between the microelectrode 140 and the wall 131 of the bore 137. In the event that the wall 131 is of a low friction material such as polytetrafluorethylene or silicone the small interstice 151 between the wall 131 and the electrode 140 can be filled with an aqueous fluid which, when freezing, can adhere to the microelectrode 140 and being withdrawn with it from the bore 137. The apparatus 130 furthermore comprises a generally U-formed conduit 134, 135, 136 disposed in the wall 131 with open ends provided with pipe sockets 132, 133 for supply and removal of a cooling fluid such as ethanol.

The lateral portions 134, 136 of the conduit are extending in parallel with the bore 137 and widening towards the upper end 139 of the cylinder wall 131; consequently, the mass of an infinitesimal horizontal wall 131 section decreases in the same direction. The cooling effect of a liquid flowing in the conduit 134, 135, 136 thus more efficiently cools upper portions of the wall 131 than lower portions, making the temperature of the wall 131 decrease from the lower end 138 towards the upper end 138' so as to form a temperature gradient. By thermal conductance the temperature gradient is transferred to a microelectrode 140 or other device disposed in the bore 137. FIG. 11a shows the apparatus 140 in a radial section M-M intermediate between the converging section 137" and the upper end 139 of the apparatus.

The microelectrode 140 of FIG. 12 is of cylindrical form with a central axis P-P. It comprises an electrically conducting core 141 of a metal such as gold or platinum. Except for its pointed 140" distal end and a distal terminal section 141' extending from the pointed end 140" in a proximal direction, the core 141 is provided with an electrically insulating coat 142 of, for instance, polyurethane, polyethylene, silicone or polytetrafluorethylene. At its proximal end 140' the microelectrode 140 is connected to controlling and/or energizing equipment (not shown) by an insulated flexible metal wire 143 fastened at the core 142 at a solder point 144.

FIG. 13 shows the microelectrode 140 fully inserted into the central bore 137 of the apparatus 130. A coolant 151 such as ethanol flows in the conduit 134, 135, 136 entering at socket 132 end leaving at socket 133. The direction of coolant 151 flow is indicated by arrows.

Example 13

The variety 171 of the microelectrode 61 of FIG. 5 shown in FIG. 15 in addition to a cylindrical electrode body 172 with a narrowing distal tip 176 and a flexible electrical lead 173 attached to its proximal end, comprises an electrically insulating layer 174 of a polymer material such as polyurethane or Parylene C covering, except for a portion 172' extending from the distal tip in a proximal direction, the electrode body 172. The insulating layer 174 and the non-insulates portion 172' of the electrode body 172 is covered by a layer 175 of dry gelatin. In the same manner as the microelectrode 61 the microelectrode 171 is provided at its proximal end with a gripping ridge for coupling of gripping claws of insertion plunger arms for displacement of the microelectrode in a distal or proximal direction. In contrast to the microelectrode 61 of FIG. 5, the gelatin layer 175 is covered, fully or partially, by a layer of ice 176, the temperature of the gelatin embedded portion of the electrode body 162 (directly or with the intermediate electrically insulating layer 164) being from 0° C. to –3° C. or to –7° C. The ice layer 176 is attached by, for instance, dipping the microelectrode 61 of FIG. 5 of a temperature of below 0° C., in particular of –3° C. or lower, in cold water, in particular into water of from +1° C. to 0° C., then withdrawing it immediately. Alternatively, a correspondingly cooled microelectrode 61 is introduced for a short time, such as for up to 10 seconds or up to 30 seconds, into a chamber filled with air or nitrogen or other suitable gas of high humidity, such as a humidity of 90% or 95% or 99% or more, the gas in the chamber being kept at a low temperature close to 0° C., such as from 0° C. to 3° C., in particular at a slightly higher temperature than the temperature of the microelectrode 61.

Example 14

FIGS. 14-14c illustrate the combination of a surgical needle 161 provided with a handle 168 at its proximal (rear) end and a cylindrical insert 163 movably disposed in the cylindrical channel 162 (axis O, FIG. 14c) of the needle 161 for implantation of a microelectrode 61 or other device of the invention in soft tissue 73. In contrast to the needle 70 of FIG. 5 the needle 161 wall is symmetrically slanting towards the channel 162 axis O in a distal direction. Near its proximal end provided with knob 165 the insert 163 comprises a radially extending stopper flange 166 restricting its insertion depth into the channel 162 so as to make the axially slanting faces of the insert tip 164 snugly fit with the axially slanting faces of the distal terminal section 161' of the needle 161 so as to provide a kind of composite or joint tip 161', 164 of the combination of needle 161 and insert 163, thereby providing for tissue friendly insertion. In the fully inserted position of the insert 163 the slanting faces of the insert 163 and the needle 161 thus form a common curved face. It is important for the interstice 167 between the insert 161 and the channel 162 wall to be sufficiently wide to provide for pressure equilibration during withdrawal of the insert 163. Another way of supporting pressure equilibration on withdrawal (not shown in the figures) is to provide a narrow channel in the insert 163 extending from a distal terminal or point face to a proximal face thereof.

The implantation of a microelectrode 61 into soft tissue 73 by means of the combination 161, 163 of needle and insert is illustrated in FIGS. 14-14d. The process is started by inserting, in a distal direction R, the combination 161, 163 with the insert 163 fully inserted into the channel 162 into soft tissue (direction of insertion F, FIG. 14). Upon reaching the desired insertion depth the insertion is stopped (FIG. 14a). Then the insert 163 is withdrawn while the needle 161 is left in the inserted position (FIG. 14b). Next, the microelectrode 61 is fully inserted into the channel 162 (FIG. 14c), then the needle 163 is withdrawn in a proximal direction R while keeping the microelectrode 61 in the inserted position by means of the gripping claws 68, 68' of the insertion plunger arms 69, 69' holding it at the co-operating ridge 67' (FIG. 14c). The terminal insertion state is reached upon the tissue 73 closing in on and holding the microelectrode 61 in place (FIG. 14d).

The variety 190 of combination of surgical needle 191 and cylindrical insert 193 of which only a distal terminal portion is shown in FIG. 17 differs from the combination 161, 163 of FIGS. 14-14c by its distal point comprising slanting co-planar distal faces 198, 199 forming a joint distal tip, its proximal portion being otherwise of same design as that of the combination 161, 163. The cylindrical outer face of the needle 191 is correspondingly provided with a layer 194 of gelatin covered by a layer 195 of ice. The interstice 197 between the needle 191 channel wall and the insert 193 must be sufficiently wide to allow easy withdrawal of the insert 193 upon implantation into nervous tissue.

Example 15

The microelectrode 171 illustrated in FIGS. 15, 15a differs from the microelectrode 61 by a layer of ice 176 disposed on the gelatin layer 175. Reference numbers 172, 172', 173 and 174 identify the electrode body and its distal terminal section, and the insulating layer, respectively. The ice layer 176 can be provided by, for instance, dipping the microelectrode 61 of a temperature substantially below 0° C. into cold water, then immediately withdrawing.

Example 16

FIGS. 16, 16a illustrate a surgical needle 181 of same kind as the needle 161 of FIGS. 14-14d. The needle 181 has a cylindrical channel 182 with a channel axis Q and is provided with a layer 184 of gelatin and, optionally in a cooled state, with a layer of ice 185 on the gelatin layer 184. This modification provides for tissue friendly insertion into soft tissue.

The invention claimed is:

1. A device for insertion into soft tissue, in particular nervous or endocrine tissue, selected from microelectrode, temperature sensor, optical sensor, optical fibre, temperature control element, microdialysis probe, comprising:

a device body extending between a distal end and a proximal end comprising a distal terminal section extending from the distal end in a proximal direction; and a layer of a material capable of forming a gel in contact with aqueous body fluid covering the distal terminal section;

wherein the distal terminal section, and the layer of material capable of forming a gel in contact with aqueous body fluid have a temperature substantially below body temperature during a period of time prior and up to insertion; and wherein the distal terminal section, and the layer of material capable of forming a gel in contact with aqueous body fluid are covered by a layer of ice.

2. The device of claim 1 in a state prior to insertion, wherein the distal portion of the device has a temperature comprised by the range of from −20° C. to 0° C.

3. The device of claim 1, wherein the temperature of the distal portion comprised by said range increases in a radial direction.

4. The device of claim 1, wherein the temperature of a proximal section of the device is lower than the temperature of the distal terminal section by 2° C. or more.

5. The microelectrode according to claim 1, wherein the device body is an electrode body of an electrically conducting material.

6. The microelectrode of claim 5, comprising a cooling means mounted at a proximal portion of the electrode body and in thermally conducting contact with it.

7. The microelectrode of claim 6, wherein the cooling means is or comprises a heat sink.

8. The microelectrode of claim 7, wherein the heat sink is of metal, in particular a metal of metal alloy of high specific weight such as copper, iron, steel, lead, chromium, nickel, silver, gold, and their alloys.

9. The microelectrode of claim 6, wherein the cooling means is or comprises a Peltier element.

10. The microelectrode of claim 9, wherein the Peltier element is mountable on the microelectrode and dismountable from the microelectrode.

11. The microelectrode of claim 6, wherein the cooling means comprises a container having a void at least partially filled with a coolant at low temperature, in particular dry ice.

12. The microelectrode of claim 11, wherein the container is closed.

13. The microelectrode of claim 11, wherein the coolant is dry ice and wherein the container void is in communication with one end of a channel disposed in the electrode body or the layer of material capable of forming a gel in contact with aqueous body fluid, the other end of the channel opening into the environment.

14. The microelectrode of claim 11, wherein the container is mountable on the electrode and dismountable from it.

15. The microelectrode of claim 1, comprised by a microelectrode bundle or array.

16. The optical sensor according to claim 1, wherein the device body is or comprises a detector of UV, visible or IR light constituting or comprised by said terminal section.

17. The temperature sensor according to claim 1, wherein the device body is or comprises a thermocouple.

18. The light conductor according to claim 1, wherein the device body is or comprises a distal terminal portion of an optical fibre.

19. The temperature control element according to claim 1, wherein the device body is an oblong metallic rod optionally comprising any of heat sink, Peltier element, container filled with coolant such as dry ice mounted at its distal end in a thermally conductive manner.

20. The microdialysis probe according to claim 1, wherein the device body is constituted by the probe which comprises an aqueous fluid conduit provided with a semi-permeable membrane section.

21. The device of claim 1, wherein the layer of a material capable of forming a gel in contact with aqueous body fluid comprises a pharmacologically active agent.

22. The device of claim 1, wherein the layer of a material capable of forming a gel in contact with aqueous body comprises two or more sub-layers differing in regard of their swelling and dissolution properties.

23. The device of claim 22, wherein an inner layer is swelling and dissolving in contact with aqueous body fluid more readily than an outer layer.

24. An assembly for insertion of the device of claim 1 into soft tissue comprising the device and a cooling means separate of the device comprising a surgical cannula or needle having a lumen, wherein the device is disposable in the lumen.

25. The assembly of claim 24, wherein the cannula comprising the device is of a temperature substantially below body temperature, such as a temperature of 30° C. or 40° C. or more below body temperature.

26. A method of inserting the device of claim 1 into soft tissue, in particular nervous or endocrine tissue, comprising:
providing a surgical cannula or needle having a lumen;
disposing the device in the lumen with its distal end facing the distal opening of the cannula;
cooling the cannula to a temperature at least 30° C. below body temperature;
inserting the cooled cannula into the tissue to a desired depth; and
expelling the device from the distal opening of the cannula then withdrawing the cannula or withdrawing the cannula while keeping the device at the desired position.

27. A method of inserting the device of claim 1 into soft tissue, in particular nervous or endocrine tissue, comprising:
providing a channel in the tissue filled with an aqueous gel of a biocompatible material, in particular gelatin;
inserting the device into the channel, for instance by means of a syringe.

28. An apparatus for cooling the device of claim 1, comprising a wall, a lower end and an upper end, a channel extending from the upper end towards the lower end and having an open upper end and a diameter adapted to receive the device by insertion with its distal end foremost, the apparatus comprising a conduit with open ends for a cooling fluid and designed for controlling the temperature of the wall in a manner to make it decrease from its lower end towards its upper end.

29. The apparatus of claim 28, wherein the conduit extends from an upper portion to a lower portion thereof.

30. The apparatus of claim 28, wherein the conduit is narrowing towards the lower end.

31. The apparatus of claim 28, wherein the mass of the wall increases towards the lower end.

32. The apparatus of claim 28, wherein the fluid is a liquid that does not solidify at temperatures above −5° C.

33. A combination of surgical cannula or needle and needle channel insert for inserting a device of the invention into soft tissue, comprising a means capable of stopping the distal displacement of the insert in the channel to provide the combination with a joint distal point comprising co-planar or co-curved faces.

34. The combination of claim 33, wherein the distal point is asymmetric.

35. The combination of claim 33, wherein the distal point is symmetric.

36. The combination of claim 33, wherein a distal portion of the needle is covered with an agent capable of forming a gel on contact with aqueous body fluid.

37. The combination of claim 36, wherein the agent capable of forming a gel on the distal portion is covered with ice.

* * * * *